United States Patent [19]

Wilk

[11] Patent Number: 5,800,334

[45] Date of Patent: *Sep. 1, 1998

[54] INTRAPERICARDIAL ASSIST DEVICE AND ASSOCIATED METHOD

[76] Inventor: Peter J. Wilk, 185 W. End Ave., New York, N.Y. 10023

[*] Notice: The term of this patent shall not extend beyond the expiration date of Pat. No. 5,533,958.

[21] Appl. No.: 678,479

[22] Filed: Jul. 9, 1996

Related U.S. Application Data

[63] Continuation-in-part of Ser. No. 286,817, Aug. 5, 1994, Pat. No. 5,533,958, which is a continuation-in-part of Ser. No. 78,567, Jun. 17, 1993, Pat. No. 5,385,528.

[51] Int. Cl.⁶ .................................................. A61B 17/12
[52] U.S. Cl. ............................... 600/18; 601/153; 604/99; 607/3
[58] Field of Search ........................ 601/151, 152, 601/153; 607/3, 5, 129, 130, 116, 119; 600/16, 17, 18; 128/639, 644; 604/96, 97, 98, 99

[56] References Cited

U.S. PATENT DOCUMENTS

| 3,587,567 | 6/1971 | Schiff . |
| 5,073,168 | 12/1991 | Danforth .................................. 604/167 |
| 5,169,381 | 12/1992 | Snyders . |
| 5,171,297 | 12/1992 | Barlow et al. . |
| 5,195,970 | 3/1993 | Gahara . |

*Primary Examiner*—Scott M. Getzow
*Attorney, Agent, or Firm*—R. Neil Sudol; Henry D. Coleman

[57] ABSTRACT

A surgical method for assisting a malfunctioning heart comprises inserting a balloon into an intrapericardial space and inflating the balloon in the intrapericardial space to place a compressive pressure on a heart in the intrapericardial space sufficient to force blood from the heart. A lubricant is fed to the intrapericardial space after insertion of the balloon into the space.

20 Claims, 4 Drawing Sheets

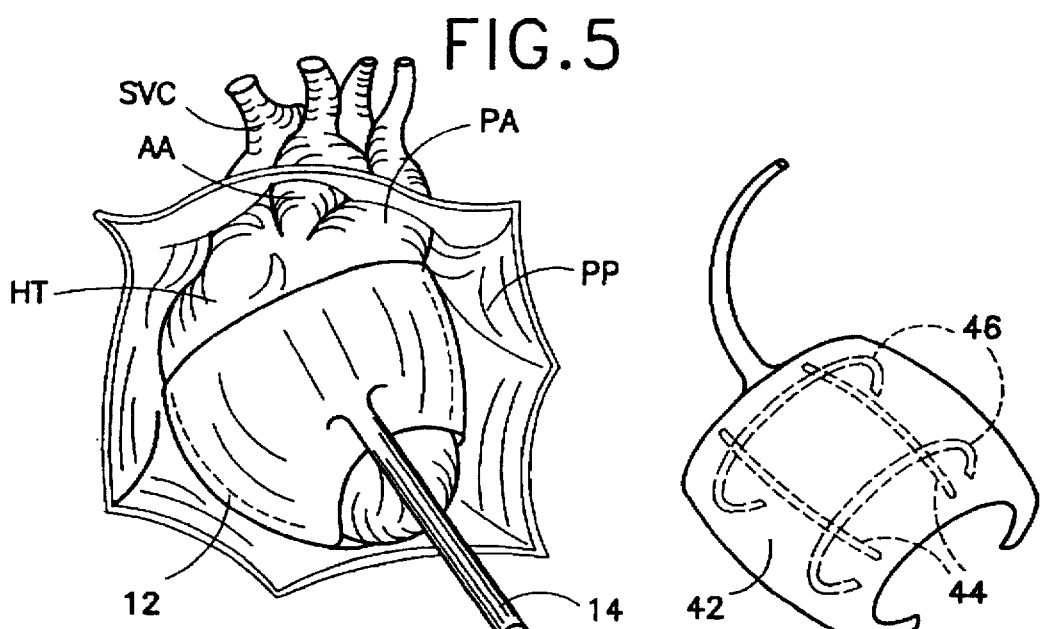
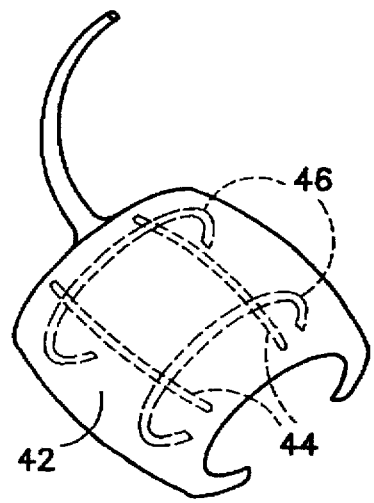
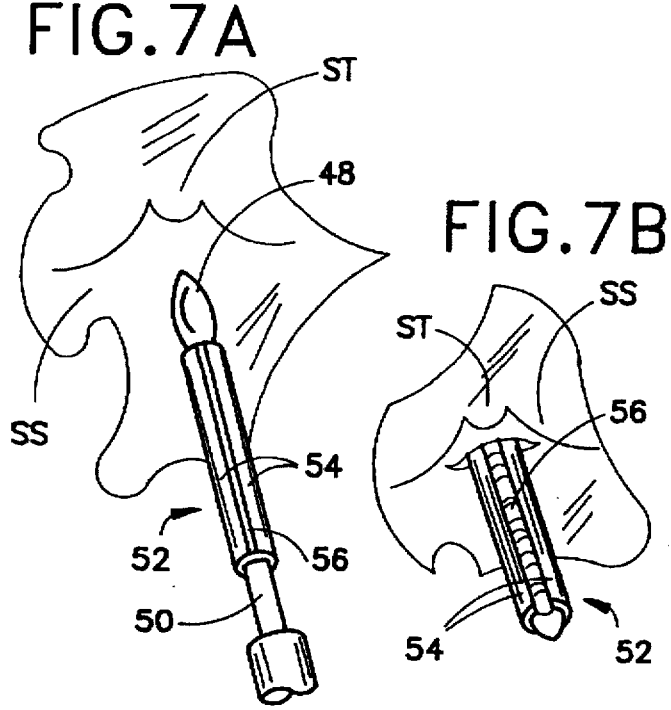
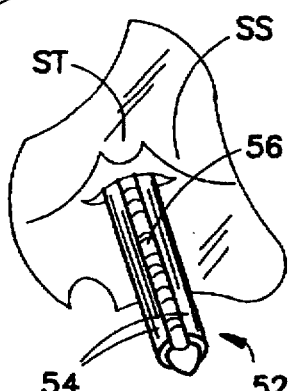
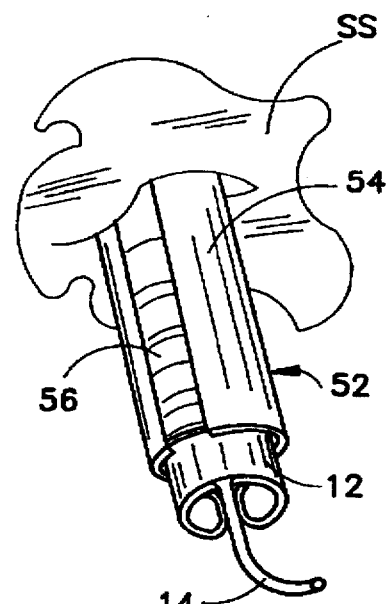

INTRAPERICARDIAL ASSIST DEVICE AND ASSOCIATED METHOD

CROSS-REFERENCE TO RELATED APPLICATIONS

This application is a continuation-in-part of application Ser. No. 08/286,817 filed Aug. 5, 1994, now U.S. Pat. No. 5,533,958, which was filed as a continuation-in-part of application Ser. No. 08/078,567 filed Jun. 17, 1993, now U.S. Pat. No. 5,385,528.

BACKGROUND OF THE INVENTION

This invention relates to an intrapericardial assist device. This invention also relates to an associated surgical method for starting a stopped heart or restarting a heart with a pronounced arrythmia.

When a patient's heart stops, for example, in the operating room, cardiopulmonary resuscitation (CPR) is required. In that procedure the chest is violently pounded at the region of the sternum to compress the chest and thereby compress the heart between the sternum and the spine. This compression forces blood out of the ventricles through the one-way valves of the heart. When the pressure on the heart is released, the heart expands and blood is sucked into the heart.

For all its violence, CPR is a delicate procedure in that it must be performed correctly in order to have the desired result of starting the stopped heart. A problem with CPR is that, whether or not it is performed correctly, CPR invariably results in cracked ribs, a fractured sternum and destroyed costo-chondral (cartilage) junctions. Thus even if a patient survives CPR, he is usually injured.

It is known to insert a needle into the intrapericardial space around the heart. This procedure is frequently undertaken to obtain a sample of fluid (e.g., blood) in the intrapericardial space. An electrical sensor at the tip of the needle senses when the surface of the heart has been reached and alerts the doctor to cease pushing on the needle.

OBJECTS OF THE INVENTION

An object of the invention is to provide a method and/or an associated device for resuscitating a stopped heart.

A more particular object of the invention is to provide such a method wherein the excessive trauma characteristic of conventional CPR is largely, if not completely, obviated.

Another object of the invention is to provide such a method which is easy and quick to use.

Another, more particular, object of the invention is to provide such a method which may be implemented at least partially automatically, thereby reducing the exertion required by the resuscitating personnel.

Yet another object of the invention is to provide a method for introducing or instilling a regular heart beat into a heart which has a pronounced and potentially fatal arrythmia.

A further particular object of the invention is to provide a device for cardiopulmonary resuscitation and/or for regularizing a heart beat.

These and other objects of the invention will be apparent from the drawings and detailed descriptions herein.

BRIEF DESCRIPTION

A surgical method for aiding a malfunctioning heart utilizes, in accordance with one embodiment of the present invention, an inflatable balloon in a collapsed configuration. The balloon is inserted into an intrapericardial space about a heart disposed in the space. Subsequently, the balloon is inflated in the intrapericardial space to place a compressive pressure on the heart sufficient to force blood from the heart. In addition, a lubricant is fed to the intrapericardial space after insertion of the balloon into the space.

Preferably, lubricant is fed to the intrapericardial space by dripping the lubricant via gravity flow. The lubricant facilitates multiple cycles of balloon expansion by reducing friction with the pericardial wall. The lubricant may be a saline solution with cortico-steroids to at least reduce adhesion formation. The balloon is made of a flexible material with a low coefficient of friction such as GORTEX$_{tm}$.

Where a pair of tubes are operatively connected to the balloon, the inflating of the ballooon includes guiding a fluid under pressure to the balloon via one tube, while the feeding of the lubricant to the intrapericardial space including guiding the lubricant to the intrapericardial space via another tube.

The inserting of the balloon into the intrapericardial space is accomplishable via a hypodermic type needle which is inserted through a skin surface and into the intrapericardial space. The balloon is injected in the collapsed configuration into the intrapericardial space.

Generally, it is contemplated that the balloon is periodically inflated and collapsed after insertion into the intrapericardial space.

The balloon may be provided with an electrode on a surface adapted for contact with the heart. In that case, the method further comprises conducting a voltage through the electrode to the heart after inflation of the balloon. Where the voltage is a defibrillating voltage, the method further comprises monitoring heart action via an EKG device for a predetermined period upon completion of the step of conducting and, upon a determination that the heart has started with an inadequate strength, inflating the balloon in synchronism with a heart contraction to place a compressive pressure on the heart to thereby increase pumping action.

Alternatively, a pacemaker type periodic voltage may be generated and applied to the heart via the electrode. The balloon is maintained in an inflated state during application of the periodic voltage to the heart to maintain the electrode in electrically conductive contact with the heart of the patient.

An intrapericardial assist device comprises, in accordance with an embodiment of the present invention, a balloon having a predetermined size and shape in an expanded configuration so that the balloon is capable of being disposed in an intrapericardial space about a heart. An inflation component is operatively connected to the balloon for inflating the balloon from an unfolded collapsed configuration to the expanded configuration. Also, a lubricating element such as a feed or drip tube is operatively connected to the balloon for delivering a lubricant to an external surface of the balloon upon disposition of the balloon in the intrapericardial space.

A spring such as an elongate rib element may be connected to the balloon for automatically unfurling the balloon from a folded collapsed configuration to an unfolded collapsed configuration.

Preferably, the inflation component includes means for automatically and periodically inflating and alternately deflating the balloon upon a disposition thereof into the intrapericardial space.

An electrical contact may be disposed on a surface of the balloon for conducting electrical energy to the heart upon an insertion of the balloon into the intrapericardial space. In that event, circuitry is operatively connected to the contact for supplying electrical energy to the contact.

A surgical method for assisting a malfunctioning heart comprises, in accordance with a general conceptualization of the invention, inserting a balloon into an intrapericardial space, and inflating the balloon in the intrapericardial space to place a compressive pressure on a heart in the intrapericardial space sufficient to force blood from the heart. Generally, the balloon is periodically inflated after insertion thereof into the pericardial space.

A method in accordance with the invention solves the problem of the trauma and injury inflicted upon a patient during conventional CPR. Ribs and sternum remain intact.

A method and apparatus in accordance with the invention serve in part to introduce a regular heart beat into a heart which has a pronounced and potentially fatal arrythmia. Pursuant to the invention, upon insertion of the electrode-carrying balloon into the intrapericardial space, the arrythmic heart is shocked by a defibrillating voltage into exhibiting a more regular heart beat. The balloon is then used to assist the heart during initial stages of its newly regular action. A pacemaker voltage is subsequently applied to the restarted heart for extending the regular action of the heart.

BRIEF DESCRIPTION OF THE DRAWING

FIG. 5 is a perspective view of the cuff of FIGS. 1–4 in an expanded configuration in place inside an intrapericardial space.

FIG. 6 is another schematic perspective view of an inflatable intrapericardial cuff in accordance with the invention, showing memory ribs inside the cuff for aiding in an unfolding thereof upon insertion of the cuff into an intrapericardial space.

FIGS. 7A–7C are schematic perspective views showing successive steps in one intrapericardial cuff insertion procedure in accordance with the invention.

DETAILED DESCRIPTION

Figure 1:
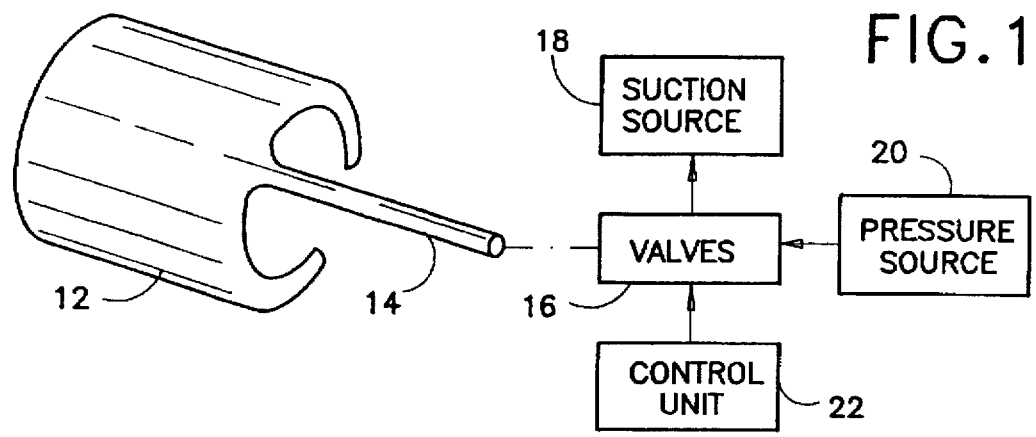
FIG. 1 is a partially a schematic perspective view, on a reduced scale, and partially a block diagram of an intrapericardial assist or resuscitation assembly in accordance with the invention, showing an inflatable intrapericardial cuff in an expanded configuration.

As illustrated in FIG. 1, an intrapericardial assist or resuscitation assembly comprises an alternately inflatable and collapsible balloon 12 in the form of a cuff. Cuff 12 has an elongate tube 14 extending to a valve device 16 which is connected to a suction source or vacuum generator 18 and to a source 20 of pressurized fluid such as water, saline solution or a gas such as air. In response to signals from a control unit 22, valve device 16 periodically connects cuff 12 to pressure source 20 and alternately to suction source 18, whereby cuff 12 is rapidly and forcefully inflated with a predetermined periodicity.

Control unit 22 may be provided with setting knobs (not illustrated) for varying the rate and maximum pressure that is applied to the cuff upon proper disposition thereof in the intrapericardial space about the heart.

Figure 2:
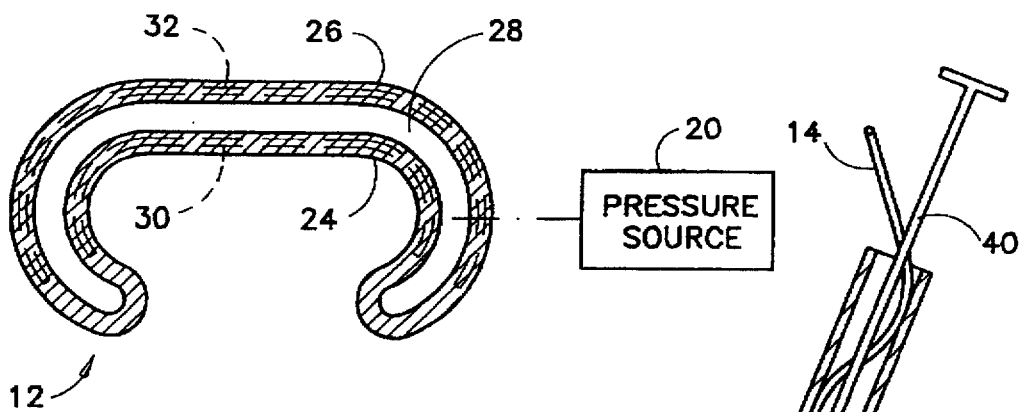
FIG. 2 is a schematic cross-sectional view of the inflatable intrapericardial cuff of FIG. 1.

As illustrated in FIGS. 1 and 2, cuff 12 has an arcuate, generally C-shaped configuration in its expanded or inflated state. Cuff 12 has a pair of major C-shaped walls 24 and 26 defining a pressurization chamber 28. Embedded in walls 24 and 26 are spring elements or ribs 30 and 32 which can be bent into a curled configuration (see FIG. 3) but which tend to resume their C-shaped expanded configurations when cuff 12 is placed into an intrapericardial space during a cardiopulmonary resuscitation procedure.

Figure 3:
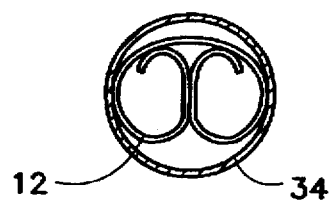
FIG. 3 is a schematic transverse cross-sectional view of the inflatable intrapericardial cuff of FIGS. 1 and 2 in a folded, collapsed pre-insertion configuration inside a hypodermic type needle.
Figure 4:
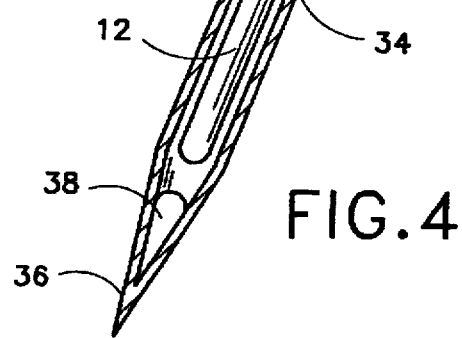
FIG. 4 is a schematic longitudinal cross-sectional view of the inflatable intrapericardial cuff of FIGS. 1–3 in the folded, collapsed pre-insertion configuration inside the hypodermic needle of FIG. 3.

As illustrated in FIGS. 3 and 4, prior to a cardiopulmonary resuscitation procedure, cuff 12 is folded and inserted in a collapsed configuration inside a hollow hypodermic type needle 34. Needle 34 is provided at a distal end 36 with an aperture 38 for the ejection of folded and collapsed cuff 12 by a distally directed stroke of a plunger member 40 upon a disposition of distal end 36 into an intrapericardial space during a cardiopulmonary resuscitation procedure. Distal end 36 is also provided with an electrical sensor for detecting the surface of the heart, as is conventional in known intrapericardial sampling needles.

Distal end 36 of intrapericardial needle 34 is inserted into the intrapericardial space through the skin under the patient sternum.

FIG. 5 shows the placement of cuff 12 in an intrapericardial space between a heart HT and the associated surrounding parietal pericardium PP. The diagram also shows the superior vena cava SVC, the pulmonary artery PA, the ascending aorta AA, and other veins and arteries.

As depicted in FIG. 6, an inflatable intrapericardial cuff 42 may be provided with a plurality of longitudinally extending ribs 44 and a plurality of transversely extending expansion ribs 46. Each rib 46 has a memory whereby the rib may be bent for insertion and retrieval from a patient's intrapericardial space, but tends to assume a pre-established configuration (FIG. 6) upon insertion of the cuff 42 into an intrapericardial space or cavity.

In another cuff insertion procedure depicted in FIGS. 7A–7C, a sharp distal tip 48 of an intrapericardial needle 50 is inserted through a patient's skin SS under the sternum ST. A dilating device 52 comprising a plurality of longitudinal ribs 54 interconnected by stretchable membranes 56 surrounds needle 50 during the insertion procedure. Upon the insertion of distal tip 48 into the intrapericardial cavity at the patient's heart, dilating device is slid in the distal direction so that a distal end portion thereof is disposed or inserted into the intrapericardial cavity. Needle 50 is then removed, as shown in FIG. 7B.

Upon the removal of needle 50 from the patient, leaving dilating device 52 partially inserted into the patient's intrapericardial cavity, the dilating device may be expanded, for example, by the insertion of a series of increasing large elongate rigid dilators (not shown). Then, cuff 12 or 42 is inserted in a folded collapsed collapsed configuration into the intrapericardial cavity through the expanded dilating device 52, as shown in FIG. 7C. An inserter (not illustrated) may be used for pushing the cuff through dilating device 52.

The general use and structure of dilating device 52 is described in detail in allowed U.S. patent application Ser. No. 851,097 filed Mar. 13, 1992 and U.S. patent application Ser. No. 893,991 filed Jun. 5, 1992. The disclosures of those applications are hereby incorporated by reference.

Figure 8:
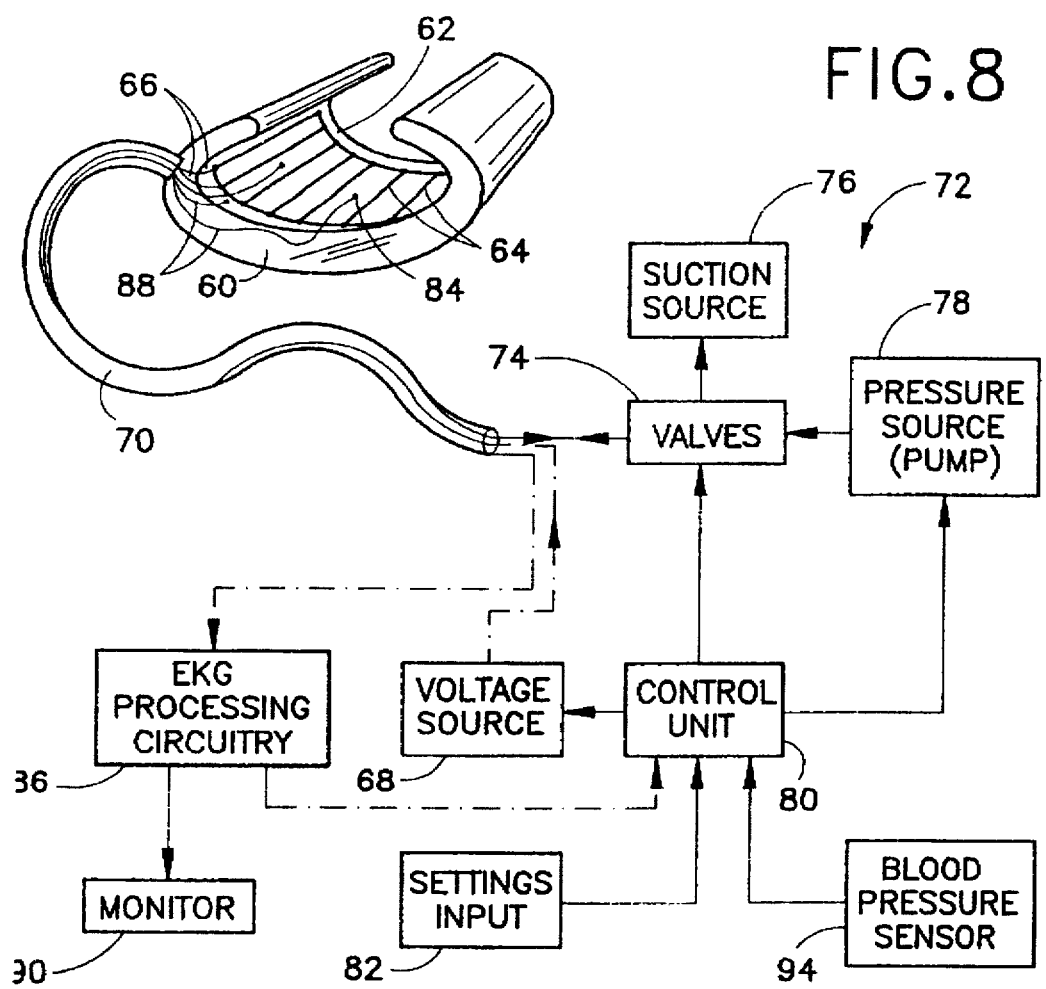
FIG. 8 is partially a schematic perspective view, on a reduced scale, and partially a block diagram of a modified intrapericardial assist or resuscitation assembly in accordance with the invention, showing an expanded intrapericardial cuff with a voltage source operatively connected to an electrode array along an inner surface of the cuff.

As depicted in FIG. 8, an intrapericardial assist device comprises an electrode carrier in the form of an inflatable balloon 60 adapted for juxtaposition to a patient's heart in an intrapericardial space, as discussed hereinabove with reference to FIG. 5. The electrode-carrying balloon 60 has an inwardly facing surface 62 adapted for contact with the patient's heart. An array of electrical contacts or electrode wires 64 is disposed on contact surface 62 of balloon 60 for conducting electrical energy to the patient's heart upon an insertion of balloon 60 into the intrapericardial space. Current transmission elements or leads 66 are operatively connected to electrical contacts 64 for delivering electrical energy thereto from a voltage source 68. A hose 70 extends to balloon 60 for maintaining the balloon in an inflated state and thereby maintaining the balloon's contact surface 62 in adequate engagement with the patient's heart during the application of electrical energy to the heart via voltage source 68, transmission leads 66 and electrical contacts or electrodes 64.

Balloon 60 is a collapsible member with a configuration of a slotted cuff in an expanded configuration. Balloon 60 has a predetermined size and shape in the expanded configuration so that it is disposable in the intrapericardial space in juxtaposition to the patient's heart. Preferably, one or more spring elements in the form of elongate ribs, e.g. 30, 32 (FIG. 2) or 44, 46 (FIG. 6), are connected to balloon 60 for automatically unfurling the balloon from a folded collapsed insertion configuration to an expanded use configuration.

The means for maintaining contact surface 62 of balloon 60 in engagement with the patient's heart during a cardiac jump start as described herein includes inflation componentry 72 operatively connected to balloon 60 via hose 70. Inflation componentry 72 includes a valve device 74 which is connected to a suction source or vacuum generator 76 and to a source 78 of pressurized fluid such as water, saline solution or a gas such as air or carbon dioxide. In response to signals from a control unit 80 such as a specially programmed microprocessor, pressure source 78 and valve device 74 pressurize balloon 60 to a predetermined pressure during an electrical cardiac stimulation procedure, whereby contacts or electrodes 64 are maintained in electrically conductive contact with a patient's heart. Alternatively, during mechanical heart stimulation as described herein, control unit 80 activates valve device 74 to periodically connect balloon 60 to pressure source 78 and alternately to suction source 76, whereby balloon 60 is rapidly and forcefully inflated with a predetermined periodicity.

Control unit 80 is provided with setting knobs 82 for enabling a preselection of an inflation pressure of balloon 60 and for varying the rate and maximum pressure that is applied to balloon 60 upon proper disposition thereof in the intrapericardial space about the heart.

As further depicted in FIG. 8, a plurality of sensor electrodes 84 is disposed on contact surface 62 of balloon 60 for monitoring natural voltages of a cardiac cycle. Sensor electrodes 84 are connected to EKG processing circuitry 86 via leads 88. According to conventional signal processing techniques, circuitry 86 generates a signal indicative of the patient's heart activity and displays the signal via a cathode ray tube (CRT) or video screen 90. Sensor electodes 84 and EKG processing circuitry facilitate the monitoring of heart activity during a heart resuscitation or beat regularization procedure as described below.

In a surgical method for reactivating a malfunctioning heart, e.g., a stopped heart or a dangerously arrythmic heart, balloon 60 is inserted into an intrapericardial space about the patient's heart, as discussed above with reference to FIGS. 5 and 7A–7C. Upon deployment of balloon 60 in the intrapericardial space, the balloon is inflated to place electrodes 64 in electrically conductive contact with the heart. Then, a defibrillating type voltage produced by a generator 92 of voltage source 68 is conducted via leads 66 and electrodes 64 to the patient's heart.

Upon the conduction of the defibrillating type voltage to the patient's heart, heart action is monitored via electrodes 84, processing circuitry 86 and CRT 90 for a predetermined period. If it is determined at that juncture that the patient's heart has started but with an insufficiently strong action, input provided to control unit 80 via setting knobs 82 induces that unit to control valve device 74 so as to inflate balloon 60 forcefully in synchronism with a heart contraction. Synchronism may be achieved, for instance, by providing control unit 80 with input from a blood pressure and pulse sensor 94 (including, e.g., a separate pressure cuff). Alternatively, if balloon 60 is sufficiently inflated, control unit 80 may receive input from EKG processing circuitry 86. In either case, control unit or microprocessor 80 determines when a heart contraction is about to occur and opens valve device 74 to induce a flow of pressurizing fluid along hose 70 to balloon 60. The placement of a compressive pressure on the heart to thereby increase pumping action may alternatively be initiated manually by providing a triggering signal to control unit 80 via setting knobs or input 82.

Balloon 60 may be at least partially deflated upon conduction of the defibrillating type voltage to the heart and prior to the monitoring of the heart action. The deflation may be only partial in the event that the heart action is monitored via sensor electrodes 84 and EKG processing circuitry 86. The deflation may be greater where the cardiac activity is determined via a conventional EKG device separate from balloon 60 and electrodes 84.

To further instill a regular heart beat, a pacemaker type periodic voltage is produced by a generator 96 included, together with generator 92, in voltage source 68. The pacemaker type voltage is applied to the patient's heart via contacts or electrodes 64 upon an inflation of balloon 60 sufficient to ensure electrically conductive engagement between the heart tissues and the electrodes. Control unit 80 regulates the pressurization of balloon 60 via valve device 74 and pressure source 78.

Figure 9:
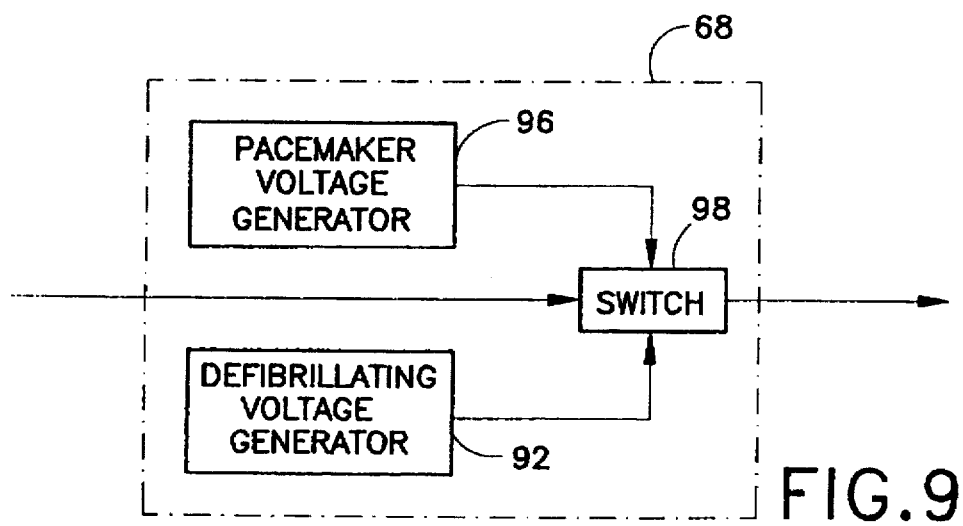
FIG. 9 is a block diagram showing details of the voltage source illustrated in FIG. 8.

The pacemaker type voltage may be applied after a defibrillating procedure as described hereinabove and after periodic cuff inflation to strengthen the heart beat. Control unit 80 determines by the activation of a switch 98 (FIG. 9) whether a defibrillating type voltage or a pacemaker voltage is applied to the cardiac tissues.

As described hereinabove with reference to FIGS. 7A–7C, the insertion of balloon 60 into the intrapericardial space may be implemented using hypodermic type needle 34. Needle 34 is inserted through a skin surface and into the intrapericardial space, balloon 60 being injected in the collapsed configuration through the needle into the intrapericardial space. As further discussed hereinabove with reference to FIGS. 7A-7C, dilating device 52 may be provided for facilitating the insertion of balloon 60 into the intrapericardial space. Needle 50 is partially inserted through the skin surface and into the intrapericardial space and a distal end portion of dilating device 52 is placed into the intrapericardial space via the needle upon the partial insertion thereof into the intrapericardial space. Dilating device 52 is subsequently expanded and balloon 60 inserted into the intrapericardial space through the expanded dilating device.

Figure 10:
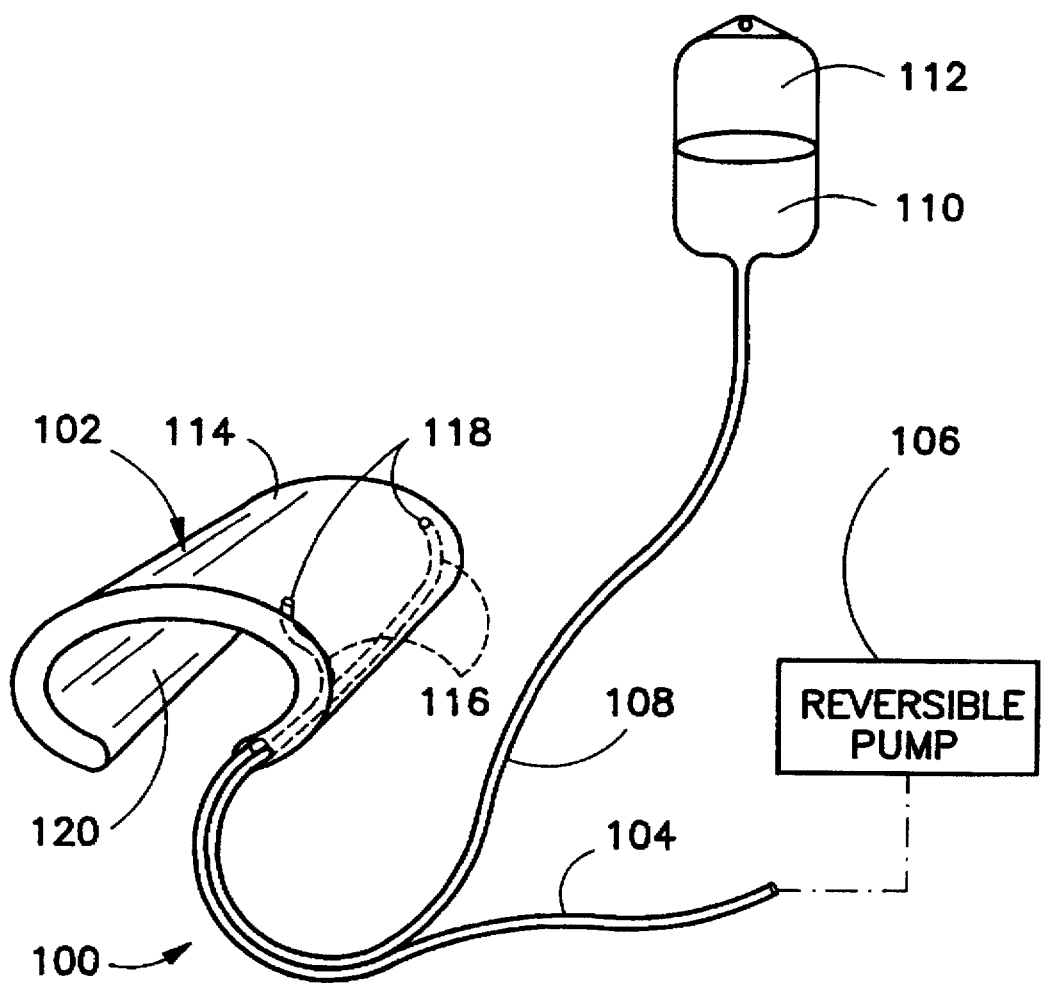
FIG. 10 is partially a schematic perspective view, on a reduced scale, and partially a block diagram of a modified intrapericardial assist or resuscitation assembly in accordance with the invention, showing an expanded intrapericardial cuff with a lubricant source operatively connected to the cuff.

As illustrated in FIG. 10, a modified intrapericardial assist device 100 comprises a balloon 102 having a predetermined size and shape in an expanded configuration so that the balloon is capable of being disposed in an intrapericardial space about a heart. Inflation componentry including a tubular member 104 and a reversible pump 106 is operatively connected to balloon 102 for inflating the balloon from an unfolded collapsed insertion configuration to the expanded configuration. Also, a feed or drip tube 108 is operatively connected to balloon 102 for delivering a lubricant 110 from a reservoir 112 to an external surface 114 of balloon 102 upon disposition of the balloon in the intrapericardial space. A manifold 116 may be provided in or along balloon 102 for delivering the lubricant 110 to a plurality of apertures or outlets 118 along surface 114. Lubricant 110 may take the form of a saline solution provided with corticosteroids for inhibiting or even preventing the formation of adhesions in the pericardial space.

The lubricating componentry of FIG. 10 may be incorporated into any of the embodiments discussed above. Conversely, componentry from the above embodiments may be added to the embodiment of FIG. 10. For example, assist device 100 may include, as shown in FIG. 2, spring elements or ribs 30 and 32 which can be bent into a curled configuration (see FIG. 3) but which tend to resume their C-shaped expanded configurations when cuff 12 is placed into an intrapericardial space during a cardiopulmonary resuscitation procedure. Spring elements or ribs 30 and 32 (FIG. 2) automatically unfurl balloon 102 (FIG. 10) from a folded collapsed configuration to an unfolded collapsed configuration.

Reversible pump 106 automatically and periodically inflates and alternately deflates balloon 102 upon a disposition thereof into the intrapericardial space. Pump 106 may include the elements illustrated in FIG. 1, namely, control unit 22, valves 16, suction source 18 and pressure source 20.

As discussed above with reference to FIG. 8, an array of electrical contacts or electrode wires 64 (FIG. 8) may be disposed on an inner contact surface 120 of balloon 102 (FIG. 10) for conducting electrical energy to the patient's heart upon an insertion of balloon 102 into the intrapericardial space. The delivery of lubricant 110 (FIG. 10) to the intrapericardial space is useful in the embodiment of FIG. 8, where a hose 70 extends to balloon 60 for maintaining the balloon in an inflated state and thereby maintaining the balloon's contact surface 62 in adequate engagement with the patient's heart during the application of electrical energy to the heart via voltage source 68, transmission leads 66 and electrical contacts or electrodes 64. Where balloon 60 must be maintained in the pericardial space for an extended period, a saline solution provided with corticosteroids is advantageously delivered to the intrapericardial space for at least inhibiting the formation of adhesions.

In assisting a malfunctioning heart with the intrapericaardial assist device 100 of FIG. 10, balloon 102 is inserted into an intrapericardial space about a heart disposed in the space. Subsequently, balloon 102 is inflated in the intrapericardial space to place a compressive pressure on the heart sufficient to force blood from the heart. In addition, lubricant 110 is fed to the intrapericardial space after insertion of balloon 102 into the space. Lubricant 110 is fed to the intrapericardial space by dripping the lubricant via gravity flow along feed tube 108. The inserting of balloon 102 into the intrapericardial space is accomplished via a hypodermic type needle 34 (FIGS. 3 and 4), as discussed above with reference to FIGS. 7A-7C. The insertion may be accomplished under direct vision, where a distal end of an endoscope (not shown) is inserted into the intrapericardial space.

It is to be noted that an intrapericardial assist balloon as described hereinabove can be used not only where a heart is stopped but also where the heart is functioning poorly. For example, where a patient is a candidate for a heart transplant, a cardiac assist balloon as disclosed herein may be implanted into the intrapericardial space for an extended period of time while the patient awaits for a donor heart.

Although the invention has been described in terms of particular embodiments and applications, one of ordinary skill in the art, in light of this teaching, can generate additional embodiments and modifications without departing from the spirit of or exceeding the scope of the claimed invention. For example, there are alternative methods for inserting a balloon type cardiac assist device into the intrapericardial space. Such alternative methods include placing the balloon through a laparoscopic cannula inserted either through the rib cage and alongside the sternum, or below the rib cage and above the diaphragm. The installation of an intrapericardial assist device may be accomplished nearly under direct vision, through a small incision beneath the ribs, without splitting any ribs.

Accordingly, it is to be understood that the drawings and descriptions herein are proffered by way of example to facilitate comprehension of the invention and should not be construed to limit the scope thereof.

What is claimed is:

1. A surgical method for aiding a malfunctioning heart, comprising:

providing an inflatable balloon in a collapsed configuration;

inserting said balloon into an intrapericardial space about a heart disposed in said space;

inflating said balloon in said intrapericardial space to place a compressive pressure on the heart sufficient to force blood from the heart; and feeding a lubricant to the intrapericardial space after insertion of said balloon into said space.

2. The method defined in claim 1 wherein said the feeding of said lubricant comprises dripping said lubricant into said intrapericardial space by a gravity flow.

3. The method defined in claim 1 wherein said lubricant is a saline solution with cortico-steroids to at least reduce adhesion formation.

4. The method defined in claim 1 wherein said balloon is made of a flexible material and has an external surface with a low coefficient of friction.

5. The method defined in claim 1 wherein a first tube and a second tube are operatively connected to said balloon, the inflating of said balloooon including guiding a fluid under pressure to said balloon via said first tube, the feeding of said lubricant to said intrapericardial space comprising guiding said lubricant to said intrapericardial space via said second tube.

6. The method defined in claim 1 wherein the inserting of said balloon includes inserting a hypodermic type needle through a skin surface and into said intrapericardial space, and injecting said balloon in said collapsed configuration into said intrapericardial space.

7. The method defined in claim 6, further comprising the step of deflating said balloon upon completion of said step of inflating, also comprising the step of again inflating said balloon upon deflation thereof.

8. The method defined in claim 1, further comprising the step of periodically inflating said balloon upon completion of said step of inserting.

9. The method defined in claim 1 wherein said balloon is provided with an electrode on a surface adapted for contact with the heart, further comprising conducting a voltage through the electrode to the heart after inflation of said balloon.

10. The method defined in claim 9 wherein said voltage is a defibrillating voltage, further comprising the steps of:

upon completion of said step of conducting, monitoring heart action via an EKG device for a predetermined period; and upon a determination that the heart has started with an inadequate strength, inflating said balloon in synchronism with a heart contraction to place a compressive pressure on the heart to thereby increase pumping action.

11. The method defined in claim 1, further comprising the steps of generating a pacemaker type periodic voltage, said step of conducting including the step of applying said periodic voltage to the heart via said electrode; and maintaining said balloon in an inflated state during said step of applying to maintain said electrode in electrically conductive contact with the heart of the patient.

12. An intrapericardial assist device comprising;

a balloon having a predetermined size and shape in an expanded configuration so that said balloon is capable of being disposed in an intrapericardial space about a heart;

inflation means operatively connected to said balloon for inflating said balloon from an unfolded collapsed configuration to the expanded configuration; and lubricating means operatively connected to said balloon for delivering a lubricant to an external surface of said balloon upon disposition of said balloon in the intrapericardial space.

13. The device defined in claim 12 wherein said lubricating means includes a tube extending to a source of lubricating fluid.

14. The device defined in claim 12, further comprising spring means connected to said balloon for automatically unfurling said balloon from a folded collapsed configuration to an unfolded collapsed configuration, said spring means being different from said inflation means, said spring means includes an elongate rib element.

15. The device defined in claim 12 wherein said inflation means includes means for automatically and periodically inflating and alternately deflating said balloon upon a disposition thereof into said intrapericardial space.

16. The device defined in claim 12 wherein electrical contact means are disposed on a surface of said balloon for conducting electrical energy to the heart upon an insertion of said balloon into the intrapericardial space, also comprising means operatively connected to said contact means for supplying electrical energy to said contact means.

17. A surgical method for assisting a malfunctioning heart, comprising the steps of:

inserting a balloon into an intrapericardial space; and inflating the balloon in said intrapericardial space to place a compressive pressure on a heart in said intrapericardial space sufficient to force blood from the heart.

18. The method defined in claim 17, further comprising the step of periodically inflating said balloon upon completion of said step of inserting.

19. The method defined in claim 17, further comprising the step of unfolding said balloon in said intrapericardial space upon insertion of said balloon into said intrapericardial space.

20. The method defined in claim 17 wherein the inserting of said balloon includes inserting a hypodermic type needle through a skin surface and into said intrapericardial space, and injecting said balloon in a collapsed configuration into said intrapericardial space.

* * * * *